United States Patent [19]
Hess et al.

[11] Patent Number: 5,630,921
[45] Date of Patent: May 20, 1997

[54] ELECTROCHEMICAL SENSOR

[75] Inventors: Charles J. Hess, Carson City; Donald R. Spriggs, Reno; Stewart Thoeni, Carson City, all of Nev.

[73] Assignee: Elsag International N.V., Amsterdam, Netherlands

[21] Appl. No.: 569,035

[22] Filed: Dec. 7, 1995

[51] Int. Cl.[6] .................................................. G01N 27/26
[52] U.S. Cl. .................................................. 204/435
[58] Field of Search .................................. 204/435, 433, 204/418, 415; 422/82.03

[56] References Cited

U.S. PATENT DOCUMENTS

| | | | |
|---|---|---|---|
| Re. 31,333 | 8/1983 | Barben | 324/450 |
| 3,264,205 | 8/1966 | Leonard et al. | 204/435 |
| 3,440,525 | 4/1969 | Cardeiro | 324/30 |
| 4,128,468 | 12/1978 | Bukamier | 204/435 |
| 4,252,124 | 2/1981 | Maurer et al. | 204/435 |
| 4,477,330 | 10/1984 | Nielsen | 204/435 |
| 4,543,175 | 9/1985 | Subsara et al. | 204/435 |
| 5,147,524 | 9/1992 | Broadley | 204/433 |
| 5,221,456 | 6/1993 | Benton et al. | 204/435 |
| 5,346,606 | 9/1994 | Christner et al. | 204/433 |
| 5,516,413 | 5/1996 | Foster et al. | 204/435 |
| 5,567,291 | 10/1996 | Melzer | 204/435 |

Primary Examiner—Bruce F. Bell
Attorney, Agent, or Firm—Michael M. Rickin

[57] ABSTRACT

An electrochemical sensor wherein an ion impermeable plug is interposed between the adjacent faces of the large plugs that are used in the salt bridge. The salt bridge also includes a solid cylindrical plug that passes through the ion impermeable plug to thereby interconnect the adjacent large plugs. The large plugs have a central bore for receiving the glass sense electrode. The impermeable plug has protrusions to provide a better seal between the impermeable plug and the glass sense electrode and the impermeable plug and the housing in which the salt bridge is inserted. In addition, the sensor may also include a rigid liner between the large plugs and the glass sense electrode to act as a barrier to prevent damage to this sense electrode during and after impregnation.

13 Claims, 2 Drawing Sheets

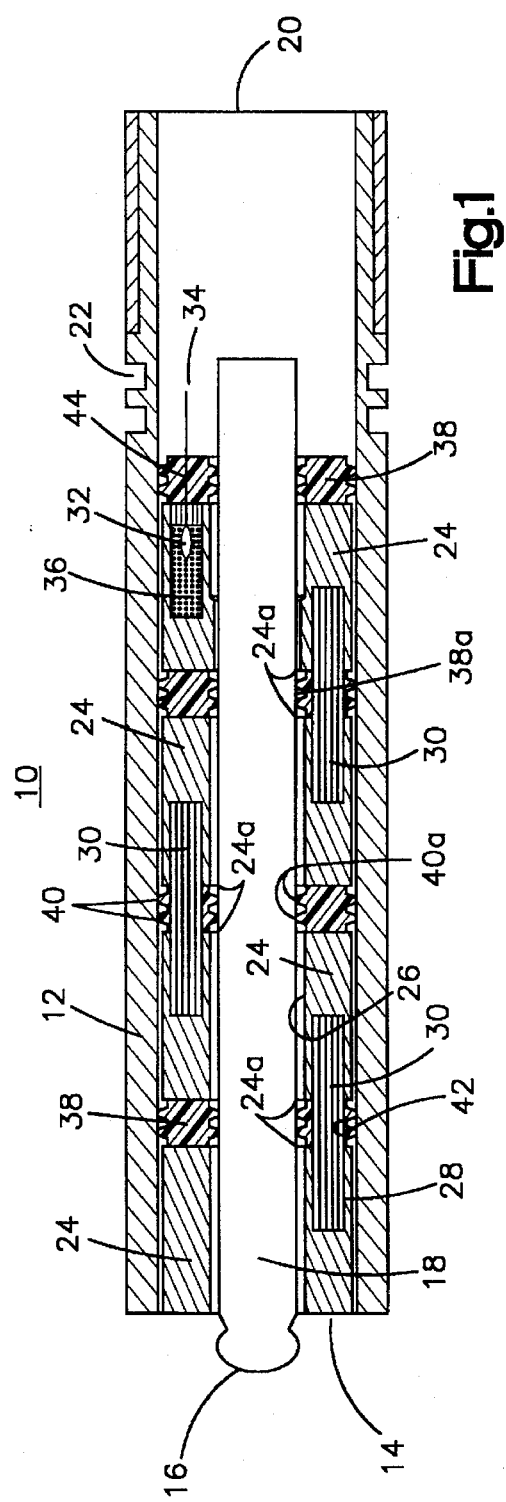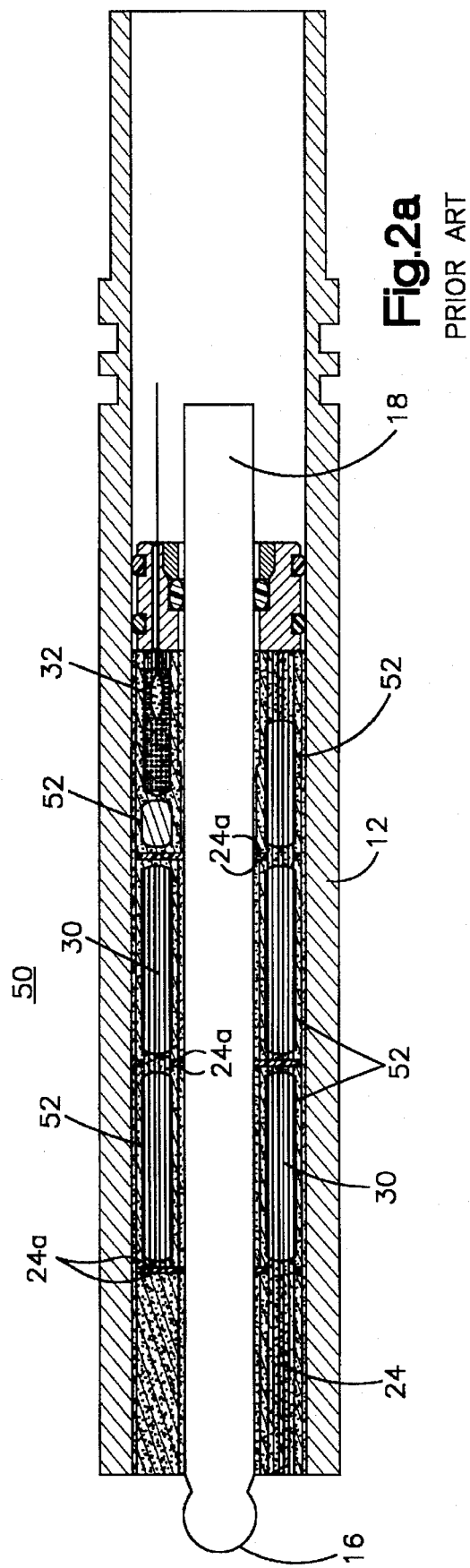

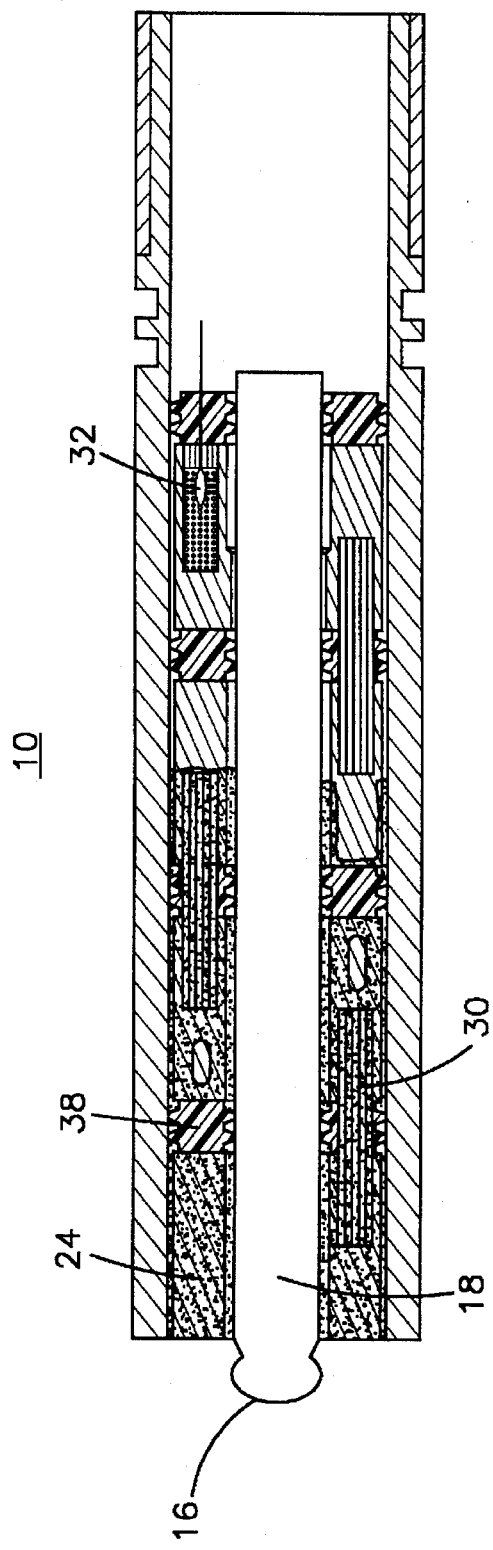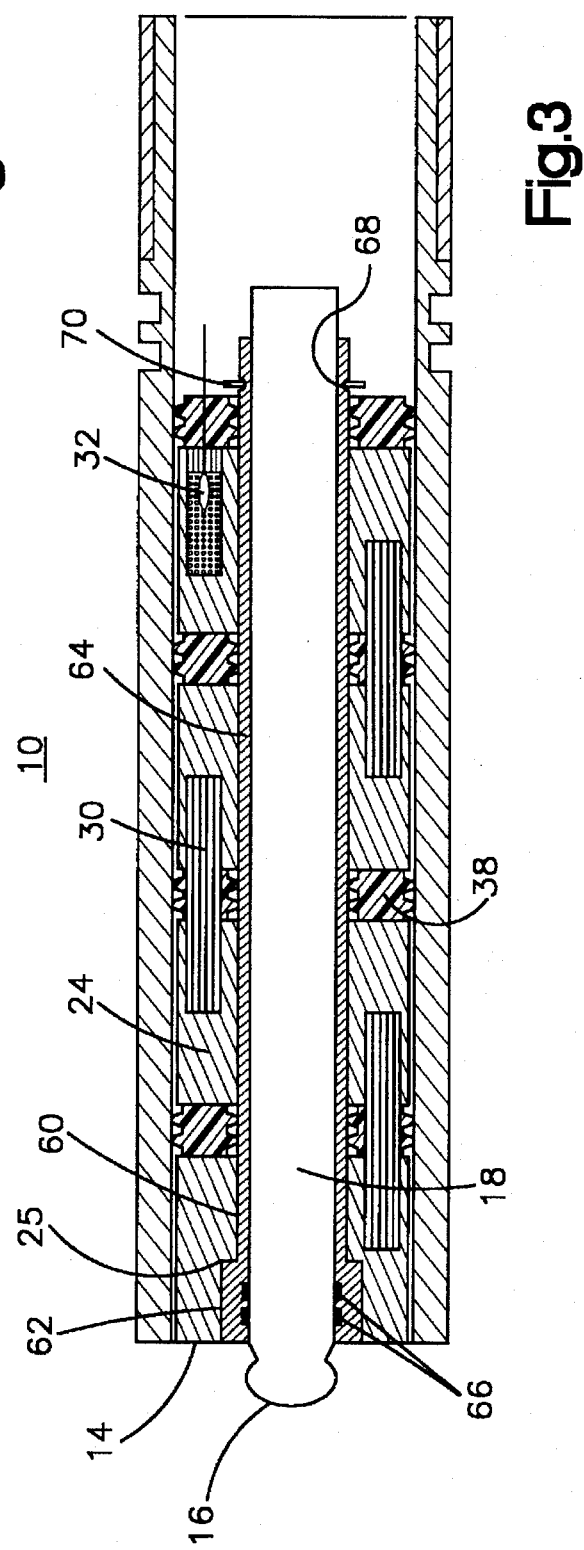

ELECTROCHEMICAL SENSOR

FIELD OF THE INVENTION

This invention relates to instruments for sensing the characteristics of a fluid, more particularly to electrochemical sensors and particularly, but not exclusively, to reference cells used in pH, ORP, or other specific ion sensors.

DESCRIPTION OF THE PRIOR ART

The reference cell used in pH, ORP, or other specific ion sensors typically utilizes a metal-metal salt (e.g., Ag/AgCl) element. In order for this reference element to maintain a common electrical potential with the specimen fluid, a suitable electrolyte in the form of a salt solution must link this element to the specimen fluid. This electrolyte provides the conductive, i.e., salt, bridge to the specimen fluid and surrounds the reference element with an electrochemically stable environment. The region where the electrolyte meets the specimen fluid is called the liquid junction and usually takes the form of a porous material.

The ideal liquid junction would provide electrolytic contact between the reference element and specimen fluid while preventing any mixing of the specimen fluid with this electrolyte. In practice, mixing is usually unavoidable and can cause undesirable effects. Thus, the liquid junction is typically the weakest point of a reference cell design.

Current liquid junction designs employ various porous material such as wood, Teflon™, ceramic frits, wicks, ground glass Joints, or even just a small hole. These junctions either separate the specimen fluid from a reservoir of electrolyte containing the reference element or are saturated with the electrolyte fluid and house the reference element in a location far removed from the specimen fluid.

A common problem with liquid junctions is maintaining a conductive path between the specimen fluid and the reference element. Liquid junctions with small openings can easily be plugged by solids contained within the specimen fluid or by crystallization of the specimen fluid with the electrolyte through some type of chemical reaction. To reduce plugging problems, large junction surfaces have been employed.

In U.S. Pat. No. 3,440,525 ("the '525 Patent") to Cardeiro, he discloses a liquid Junction that employs a large junction surface created by a single wood or porous ceramic plug. The structures of these materials maintain electrolyte contact through small capillaries extending longitudinally between the specimen fluid and reference electrolyte. The liquid junction of the '525 Patent possesses a very high density of electrically conductive salt links to the specimen fluid via the capillary structure of the wood or ceramic plug.

Another common difficulty with reference cell designs is isolating the reference element from the specimen fluid. As the specimen fluid penetrates into the liquid junction and electrolyte reservoir, the electrolyte concentration decreases and will eventually cause the potential produced by the reference cell to drift. With time, the potential will reach levels too large for calibration methods. If the specimen fluid reaches the reference element, poisoning of this element can occur, causing the reference potential to become unstable. Since these are undesirable effects, the design of the reference cell should minimize or eliminate the exchange of electrolyte with specimen fluid.

In U.S. Pat. No. Re. 31,333 ("the '333 Patent") to Barben, he discloses the use of multiple plugs of semipermeable material, such as wood, with longitudinal capillaries extending from one end of the plug to the other. These plugs are linked through a series of smaller plugs. The '333 Patent teaches that an epoxy resin or other adhesive sealant should be used to seal the abutting end surfaces of the large plugs prior to assembly of the reference cell described therein. According to the '333 Patent this use of the sealant causes the ion transfer path to be longitudinally and transversely linked between each plug.

Each of the large plugs has a pair of side apertures which are axially displaced on opposite sides of the plug's central bore. The side apertures are used to receive the smaller plugs which are inserted midway into one of the side apertures in successive pairs of the large plugs on opposite sides of the central bore. The '333 Patent teaches that the sealant fills the intervening spaces within the side apertures to seal off the fluid path between successive smaller plugs on each side. Therefore, the '333 Patent teaches that the combination of large and small plugs and sealant provides a circuitous path for ion transfer.

According to the '333 Patent, after the large and small plugs are assembled, placed in a cylindrical container along with a central glass electrode and the sealant has cured, the entire structure is immersed in a bath containing the reference cell electrolyte or salt bridge solution until the wood is thoroughly impregnated with this solution throughout the entire length of the container. The '333 Patent teaches that the absorption of the salt bridge solution into the reference cell structure causes swelling of the large and small wood plugs. This swelling causes the wood to expand in the transverse direction which causes the plugs to tightly press against one another, the central glass electrode and the inside of the rigid cylindrical container used to house the cell. While not expressly stated in the '333 Patent, this swelling of the wood would lead one skilled in the art to presume that there would be very little if any ion transfer in that part of each plug adjacent to the glass electrode and cylindrical container.

In practicing the invention taught in the '333 Patent, epoxy has also been used to seal the outside surface of each of the large plugs. It was believed that using the epoxy on the outside surface would further ensure that there would not be any ion transfer along a path through the outside surface of each plug.

Reference cells constructed in accordance with the teachings of the '333 Patent have been and continue to be used successfully in the continuous monitoring of process streams. One such application is in the monitoring of process streams wherein sulfides are present. Such streams may occur in petrochemical processes, flue gas scrubbers, and waste water treatment. The presence of sulfides in these streams has been shown to shorten the life of a reference cell. As sulfides penetrate into the reference cell structure and come in contact with the metal ions involved in the reference cell reaction (e.g., silver), an insoluble sulfide salt forms and precipitates out of solution. Since maintaining a constant reference cell potential relies on the equilibrium established between the metal and metal ions in the reference cell (i.e., the reference cell reaction), the irreversible reaction with sulfide ions depletes all of the available metal ions. Without any appreciable metal ions, the reference cell will not be well behaved and will render the sensor useless. Reference 'poisons' like sulfides can only be controlled by preventing or restricting these ions from making direct contact with the reference element.

While a reference cell constructed in accordance with the teachings of the '333 Patent has been found to have a longer life than other known reference cells, sealing weaknesses with the region between the glass electrode, cylindrical container, and adjoining surface of the large wood plugs have been observed using a dye solution.

Poor sealing against the glass electrode relates to the manufacturability of the device. Since the swelling of the wood plugs within the reference cell is highly unpredictable, ensuring a reliable and reproducible seal between the glass electrode and wood plugs is quite difficult. If inadequate spacing is used between these components, the final product yields either a sensor with a broken glass electrode and an unusable device or a sensor with inadequate sealing and shortened sensor life. The same situation occurs with the sealing area between the wood plugs and cylindrical container.

Finally, the seals between each large wood plug are compromised during the impregnation process. Due to the rougher surface typical of end cuts across the wood grain, any delamination between the sealant (i.e., epoxy) and large wood plugs creates open channels.

Though these weaknesses have not greatly impacted sensor life in most applications, a reference cell that has an increased life when used in the monitoring of process streams where sulfides are present is desirable.

Additionally, most measurement cells (i.e., electrodes) have a tubular, glass construction. The compressive loading resulting from the swelling of the large wood plugs would in theory be evenly distributed over the circular structure of the tubular glass electrode. Since most glass materials possess very good compressive strength it would then be expected that the electrode could handle such compressive loading. Unfortunately, the swelling is not uniform from plug to plug or from side to side on a sole plug. Thus, the loads placed on the glass electrode typically are in the form of both compressive and shear.

Such loading may cause breakage of the glass electrode when a sensor that uses porous material in its liquid junction design is placed into service in process streams having elevated temperatures, pressures and/or containing harsh chemicals. Examples of such sensors are those shown in the '333 Patent and also in U.S. Pat. No. 5,147,524 ("the '524 Patent") and U.S. Pat. No. 5,346,606 ("the '606 Patent"). The heat, pressure and/or chemicals may cause the porous material to expand and fracture the glass electrode. Therefore, it is desirable to strengthen the sensor to thereby eliminate this cause of glass electrode fracture and thus allow a sensing device to be provided having a consistent quality and performance.

SUMMARY OF THE INVENTION

The present invention is embodied in a device for use in connection with measuring ionic properties in a specimen fluid. The device has a salt bridge which is made up of a first longitudinal series of semipermeable plugs impregnated with an electrolyte; and a second longitudinal series of semipermeable plugs impregnated with an electrolyte. The first and said second series of semipermeable plugs are disposed in a longitudinally overlapping relationship with an interlocking fit.

The device also has a series of impermeable plugs. Each of the impermeable plugs are associated with a pair of adjoining transverse end surfaces of the first series of plugs and are interposed therebetween. A plug in the second series of plugs passes through each of the impermeable plugs to thereby provide an ion path between the adjoining transverse end surfaces.

The present invention is also embodied as a device for use in connection with measuring ionic properties in a specimen fluid that has a salt bridge wherein the first longitudinal series of semipermeable plugs has at least two plugs and the second longitudinal series of semipermeable plugs has at least one plug. The first and second series of plugs are disposed in a longitudinally overlapping relationship with an interlocking fit. The device also includes a series of impermeable plugs having at least one plug associated with adjoining transverse end surfaces of the at least two plugs in the first series and is interposed therebetween. The at least one plug in the second series passes through the at least one impermeable plug to thereby provide an ion path between the adjoining transverse end surfaces.

The present invention is further embodied as a device for use in connection with measuring ionic properties in a specimen fluid that has a salt bridge. The salt bridge has first and second longitudinal semipermeable plugs impregnated with an electrolyte; and a third longitudinal semipermeable plug impregnated with an electrolyte. The first, second and third plugs are disposed in a longitudinally overlapping relationship with an interlocking fit. The device further has an impermeable plug interposed between adjoining transverse end surfaces of the first and second semipermeable plugs. The third semipermeable plug passes through the impermeable plug to thereby provide an ion path between the adjoining transverse end surfaces.

The present invention is also embodied as an electrochemical sensor. The sensor has a reference electrode; a sensing electrode; a rigid liner; and a salt bridge. The salt bridge has a plug made of semipermeable material saturated with an electrolyte. The plug has a central axial bore for holding the rigid liner therein. The rigid liner has a central axial bore for holding the sensing electrode therein.

The present invention is also further embodied as an electrochemical sensor. The sensor has a semipermeable plug impregnated with an electrolyte. The plug has a central bore and axially separated first and second ends and functions as a salt bridge. The sensor further has a rigid liner in the axial bore; a sensing electrode positioned at the first end and adapted to contact a specimen fluid; and a reference electrode positioned at the second end.

DESCRIPTION OF THE DRAWING

FIG. 1 shows a cross sectional view of a sensor embodied in accordance with one aspect of the present invention.

FIG. 2a shows a cross sectional view of a sensor constructed in accordance with the teachings of the '333 Patent at the end of the ink test.

FIG. 2b shows a cross sectional view of the sensor shown in FIG. 1 at the end of the ink test.

FIG. 3 shows a cross sectional view of the sensor of FIG. 1 including a rigid liner in accordance with another aspect of the present invention.

DESCRIPTION OF THE PREFERRED EMBODIMENT(S)

Referring now to FIG. 1, there is shown a cross sectional view of a sensor 10 embodied in accordance with the life expectancy increasing features of the present invention. For ease of description, the embodiment of the sensor shown in FIG. 1 will be referred to hereinafter as a "sensor." The sensor may be used for measuring pH, ORP or specific ions in a specimen fluid (not shown).

As shown, the sensor 10 includes a housing 12 which is preferably cylindrically shaped. Typically, housing 12 is formed with high density polyvinylidene fluoride plastic or other material that has the desired structural rigidity and is inert or otherwise chemically compatible with the specimen fluid. The housing 12 has a first end 14, and the bulb 16 of a conventional glass sensing electrode 18 protrudes from the first end 14 to contact the specimen fluid for measuring, for example, the pH of the specimen fluid.

FIG. 1 also shows that the housing 12 has a second end 20, and that a coupling sleeve (not shown) and the O-ring glands 22, can be used to seal the second end 20 from the specimen sample, and that this coupling sleeve provides for the necessary engagement with a complementary fitting (not shown) on a pipe, tank, or other vessel that holds the specimen fluid. As is well known, electrical leads (not shown) are attached to the glass sensing electrode 18 and reference electrode 32 and extend outwardly from the second end 20. The electrical leads are for attachment to a suitable device, for example, a pH meter, which can process the signal generated by the sensor 10 and indicate the pH of the specimen fluid. As is also well known, the second end 20 is fill with a potting material (not shown) suitable for the type of environments typical for this device. The potting establishes a seal between the electrical leads, rear of button 38 and housing 12.

As is also shown in FIG. 1, two overlapping series of interlocking plugs fill the interior of the housing 12 surrounding the glass electrode 18. In the specific embodiment illustrated, the first series consists of four thick walled hollow cylindrical or annular shaped larger plugs 24 that fit snugly within the housing 12. Each of the plugs 24 have a central bore 26 that slidably receives the axially disposed glass electrode 18 at the center of the housing. Each of the adjoining surfaces 24a of plugs 24 also has a single longitudinally extending side aperture 28 axially displaced on one side of the central bore 26. The aperture 28 only extends about halfway through each plug.

The second series of plugs 30 are the three solid cylinders that are slidably insertable into the side apertures 28 of adjacent pairs of the plugs 24. The plugs 30 have approximately the same longitudinal dimensions as the plugs 24 for insertion midway into the side apertures 28 thus overlapping the longitudinal extent of adjacent pairs of plugs 24. Only one plug 30 is used between each adjacent pair of plugs 24 with successive ones on alternate sides of the central bore 26.

The sensor includes a reference electrode or element 32 that has an electrical lead 34 which accompanies the electrical lead of the sensing glass electrode 18. The plug 24 closest to second end 20 may include a cavity 36 for receiving the reference element 32. The reference electrode 32 is typically a conventional silver-silver chloride or calomel type electrode. The plugs 24 and 30 are saturated, that is, impregnated, with an appropriate electrolyte such as a saturated salt solution. This saturation allows electrical communication to be established through the plugs 24 and 30 between the reference electrode 32 and the specimen fluid in which the bulb 16 of the measurement electrode 18 is immersed.

A comparison of the '333 Patent with the description above of the sensor of the present invention would show that the description above also essentially describes the sensor shown in the '333 Patent. There are differences between the sensor described in the '333 Patent and the sensor of the present invention. For example, in the sensor described in the '333 Patent each of the larger plugs has a pair of longitudinally extending side apertures completely therethrough while the sensor described herein has the longitudinally extending apertures 28 only partway through the plug 24. The '333 Patent describes and shows a set of cylindrical plugs which are about twice as long as the plugs 30 described herein.

There are additional and more significant differences between the sensor described in the '333 Patent and the sensor of the present invention. As was previously described herein, the '333 Patent teaches that an epoxy resin or other adhesive sealant should be used to seal the abutting end surfaces of the plugs 24 prior to assembly of the sensor. As was further previously described herein, the '333 Patent teaches that the sealant fills the intervening spaces within the side apertures 28 to seal off the fluid path between successive smaller plugs 30 on each side of the larger plugs 24. As was also previously described herein, in practicing the invention taught in the '333 Patent, epoxy has also been used to seal the outside surface of each of the large plugs 24.

Referring once again to FIG. 1, it can be seen that in the sensor of the present invention adjacent end surfaces of the plugs 24 are separated from each other by a "button" 38 fabricated from an impermeable material. The second end 20 of the sensor is sealed by a button 38. Each button 38 includes a pair of semicircular protrusions 40 by which an O-ring type seal is provided against the housing 12. All of the buttons 38 have a central bore 38a for slidably receiving the glass electrode 18. This central bore has a pair of semicircular protrusions 40a similar to protrusions 40 to thereby provide an O-ring type seal with the glass electrode 18.

The three buttons 38 which separate the adjacent end surfaces of the plugs 24 each further include a single longitudinally extending side channel 42 completely therethrough for receiving the associated plug 30. The side channel 42 provides limited clearance of the associated plug 30 so that the squeeze created from the semicircular protrusions 40 and 40a causes channel 42 to tightly squeeze against the associated plug 30. The button 38 which seals the second end 20 does not include channel 42 but does include a single longitudinally extending side channel 44 completely therethrough for receiving the electrical lead 34 of the reference electrode 32. In one embodiment of the present invention, the impermeable material used to fabricate the buttons 38 is VITON® rubber which is available from E. I. Du Pont De Neumors & Co.

In order to determine if a sensor embodied as shown in FIG. 1 would have a longer life than a sensor constructed in accordance with the teaching of the '333 Patent, the two sensors were tested at the same time and identically. Using an apparatus that cyclically applies air pressure to the center opening of a piping tee filled with an ink solution, sensor life can be inferred by comparing the penetration of the ink solution into each sensor over a period of a few days. At the end of each test, both sensors including wooden plugs were longitudinally cut open.

Referring now to FIGS. 2a and 2b, there is shown in FIG. 2a a cross sectional view of a sensor 50 constructed in accordance with the teachings of the '333 Patent at the end of the ink test and in FIG. 2b a cross sectional view of the sensor 10 shown in FIG. 1 also at the end of the ink test. The results of the ink test for both sensors is shown in FIGS. 2a and 2b by the dark shading, which represents the ink stains, on the plugs 24 and 30.

As can be seen in FIG. 2a, the ink stains on the plugs 24 in the sensor 50, and a variation (not shown) of the sensor 50 wherein an elastomeric sealant was used around the wood reference structure, showed that the ion transfer path was either on the inside of each plug 24 adjacent to the glass electrode 18/elastomeric sealant or on the outside surface of each plug 24 adjacent to the housing 12/elastomeric sealant. Ink stains were absent in the central portion 52 of the reference cell for sensor 50. Additionally, a great deal of staining was apparent in the regions between the epoxy and the adjoining surfaces 24a of the large wood plugs 24. Apparently the swelling of the plugs during impregnation by the salt solution caused the epoxy on the outside surfaces to crack and/or delaminate.

As can be seen in FIG. 2b, the ink stains in sensor 10 showed a uniformed progression leading from the specimen fluid contact point through each of the large and small plugs 24 and 30. Staining showed complete saturation of each large plug 24 before any appreciable staining was observed in the next adjacent large plug 24. Thus, the ink stains in the sensor 10 of the present invention and the sensor 50 of the '333 Patent prove that if the '333 Patent sensor or its modified form (i.e., with elastomeric sealant) had been used in a sulfide application its reference cell would have been poisoned much sooner than the reference cell of the sensor 10.

As previously described herein, inadequate clearances between the cylindrical housing 12 and glass electrode 18 of the sensor 10 or the sensor 50 or even sensors embodied in accordance with the teachings of the '524, 525 and '606 Patents can give rise to either a sensor with a broken glass electrode or a sensor with inadequate sealing and shortened life. Referring now to FIG. 3, there is shown a cross sectional view of a further embodiment of sensor 10 which includes a rigid tubular liner 60 around the glass electrode 18. As is shown in FIG. 3, the wall 64 of the rigid liner 60 is thicker in portion 62 adjacent to first end 14 then elsewhere. The increased wall thickness in portion 62 allows for the use of standard size O-rings 66 which provides a seal to prevent the specimen fluid from reaching the potted electrical leads and aid in retaining the glass electrode 18.

Each of the large plugs 24 must be reduced slightly in diameter as compared to their diameter in the sensor shown in FIG. 1 in order to accommodate liner 60. In addition and as is shown in FIG. 3, the portion of the plug 24 which is closest to end 14 must have a step 25 therein which is complementary to portion 62. The rigid liner 60 has a groove 68 which is used to accommodate a snap ring 70. The snap ring 70 retains the assembly made up of plugs 24, 30, buttons 38, liner 60 and O-rings 66. This allows the glass electrode 18 to be inserted into that assembly just prior to shipment of the sensor 10.

It should be appreciated that the use of rigid liner 60 around glass electrode 18 minimizes the clearances between the large wood plugs 24, cylindrical housing 12, and cylindrical liner 60 without any concern that the glass electrode will be fractured after impregnation of the sensor. The smaller clearances will greatly enhance sealing between the cylindrical housing and the rigid liner and also give rise to a consistent quality and performance of the sensor 10.

In one embodiment for the sensor shown in FIG. 3, the rigid liner 60 was constructed from either stainless steel or titanium. The rigid liner may, however, be constructed from any material that can withstand the shear stresses that may result when the sensor is impregnated and later placed into service in process streams having elevated temperatures, pressures and/or containing harsh chemicals. An advantage of using an electrically conductive material for the liner is in those applications which require a solution ground. In such applications the ground can easily be provided by connecting a wire (not shown) to the snap ring 70.

Liner 60 has been shown in FIG. 3 in combination with sensor 10 of FIG. 1. It should, however, be appreciated that the liner may also be used with sensor 50 of FIG. 2a or any other type of sensor which uses a porous material in its liquid junction and has an electrode that may fracture under shear stresses.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A device for use in connection with measuring ionic properties in a specimen fluid, which comprises:
   (a) a salt bridge comprising:
      i. a first longitudinal series of semipermeable plugs impregnated with an electrolyte; and
      ii. a second longitudinal series of semipermeable plugs impregnated with an electrolyte; said first and said second series of semipermeable plugs disposed in a longitudinally overlapping relationship with an interlocking fit; and
   (b) a series of impermeable plugs, each of said impermeable plugs associated with a pair of adjoining transverse end surfaces of said first series of semipermeable plugs and interposed therebetween, a semipermeable plug in said second series of plugs passing through each of said impermeable plugs to thereby provide an ion path between said adjoining transverse end surfaces.

2. The device of claim 1 further comprising a sensing electrode and wherein each of said semipermeable plugs in said first series of plugs and each of said impermeable plugs has a central bore for slidably receiving said sensing electrode.

3. The device of claim 2 wherein each of said impermeable plugs has means for providing a seal with said sensing electrode.

4. The device of claim 2 further comprising a housing for receiving said salt bridge, said series of impermeable plugs and said sensing electrode.

5. The device of claim 4 wherein each of said impermeable plugs has means for providing a seal with said housing.

6. The device of claim 5 wherein each of said impermeable plugs has means for providing a seal with said sensing electrode.

7. The device of claim 2 further comprising a rigid liner, said central bore of said semipermeable plugs in said first series of plugs for holding said rigid liner, and said rigid liner having a central bore for holding said sensing electrode therein.

8. A device for use in connection with measuring ionic properties in a specimen fluid, which comprises:
   (a) a salt bridge comprising:
      i. a first longitudinal series of semipermeable plugs having at least two plugs impregnated with an electrolyte; and
      ii. a second longitudinal series of semipermeable plugs having at least one plug impregnated with an electrolyte; said first and said second series of semipermeable plugs disposed in a longitudinally overlapping relationship with an interlocking fit; and
   (b) a series of impermeable plugs having at least one plug associated with adjoining transverse end surfaces of said at least two plugs in said first series of plugs and interposed therebetween, said at least one plug in said second series of plugs passing through said at least one impermeable plug to thereby provide an ion path between said adjoining transverse end surfaces.

9. A device for use in connection with measuring ionic properties in a specimen fluid, which comprises:
(a) a salt bridge comprising:
  i. first and second longitudinal semipermeable plugs impregnated with an electrolyte; and
  ii. a third longitudinal semipermeable plug impregnated with an electrolyte; said first, second and third semipermeable plugs disposed in a longitudinally overlapping relationship with an interlocking fit; and
(b) an impermeable plug interposed between adjoining transverse end surfaces of said first and second semipermeable plugs, said third semipermeable plug passing through said impermeable plug to thereby provide an ion path between said adjoining transverse end surfaces.

10. An electrochemical sensor, comprising:
(a) a reference electrode;
(b) a sensing electrode;
(c) a rigid liner; and
(d) a salt bridge comprising a plug made of semipermeable material saturated with an electrolyte, said plug having a central axial bore for holding said rigid liner therein, said rigid liner having a central axial bore for holding said sensing electrode therein.

11. The electrochemical sensor of claim 10 wherein said plug also has an impermeable barrier therein.

12. An electrochemical sensor, comprising:
(a) a semipermeable plug impregnated with an electrolyte, said plug having a central bore and axially separated first and second ends and functioning as a salt bridge;
(b) a rigid liner in said axial bore;
(c) a sensing electrode positioned at said first end and which contacts a specimen fluid; and
(d) a reference electrode positioned at said second end.

13. The electrochemical sensor of claim 12 wherein said semipermeable plug has an impermeable barrier therein.

* * * * *